(12) United States Patent
Simpson et al.

(10) Patent No.: US 10,426,846 B2
(45) Date of Patent: Oct. 1, 2019

(54) OLIG1 MINI-PROMOTERS: PIE305

(71) Applicant: The University of British Columbia, Vancouver (CA)

(72) Inventors: Elizabeth M. Simpson, Vancouver (CA); Charles de Leeuw, Seattle, WA (US); Wyeth W. Wasserman, Vancouver (CA); Daniel Goldowitz, Port Moody (CA)

(73) Assignee: University of British Columbia, Vancouver, BC (CA)

( * ) Notice: Subject to any disclaimer, the term of this patent is extended or adjusted under 35 U.S.C. 154(b) by 0 days.

(21) Appl. No.: 15/969,497

(22) Filed: May 2, 2018

(65) Prior Publication Data
US 2018/0318449 A1    Nov. 8, 2018

Related U.S. Application Data

(60) Provisional application No. 62/501,809, filed on May 5, 2017.

(51) Int. Cl.
| | | |
|---|---|---|
| *C07H 21/04* | (2006.01) | |
| *A61K 31/70* | (2006.01) | |
| *A61K 48/00* | (2006.01) | |
| *C12N 15/63* | (2006.01) | |
| *C12N 15/86* | (2006.01) | |
| *A01K 67/00* | (2006.01) | |

(52) U.S. Cl.
CPC ...... *A61K 48/0066* (2013.01); *A61K 48/0008* (2013.01); *A61K 48/0058* (2013.01); *A61K 48/0083* (2013.01); *C12N 15/86* (2013.01); *C12N 2750/14143* (2013.01); *C12N 2830/008* (2013.01)

(58) Field of Classification Search
CPC ............ A61K 48/0066; A61K 48/0008; A61K 48/0083; A61K 48/0058; C12N 15/86; C12N 2750/14143; C12N 2830/008
See application file for complete search history.

(56) References Cited

U.S. PATENT DOCUMENTS 8,629,261 B2 *    1/2014    Simpson et al.

OTHER PUBLICATIONS

Alam et al. Lung surfactant protein B promoter function is dependent on the helical phasing, orientation and combinatorial actions of cis-DNA elements. Gene 282:103-111, (Year: 2002).*
Xie et al. Domains of the rat rDNA promoter must be aligned stereospecifically. Molecular and Cellular Biology 12:1266-1275, (Year: 1992).*
Friedli et al., "A Systematic Enhancer Screen Using Lentivector Transgenesis Identifies Conserved and Non-Conserved Functional Elements at the Olig1 and Olig2 Locus." PLoS ONE, Dec. 2010, pp. 1-13, vol. 5, Issue 12, e15741, PLOS ONE, San Francisco, CA.
Gong et al., "Olig1 is downregulated in oligodendrocyte progenitor cell differentiation", Neuroreport, Aug. 6, 2008, pp. 1203-1207, vol. 19, Issue 12, Wolters Kluwer Health, Inc., Philadelphia, PA.

* cited by examiner

*Primary Examiner* — Quang Nguyen
(74) *Attorney, Agent, or Firm* — Pamela J. Sherwood; Bozicevic, Field & Francis LLP

(57) ABSTRACT

Isolated polynucleotides comprising an OLIG1 mini-promoters are provided. The mini-promoter may be operably linked to an expressible sequence, e.g. reporter genes, genes encoding a polypeptide of interest, guide RNA, regulatory RNA sequences such as miRNA, siRNA, anti-sense RNA, etc., and the like. The promoter may also be provided in a vector, for example in combination with an expressible sequence. The polynucleotides find use in a method of expressing a sequence of interest, e.g. for identifying or labeling cells, monitoring or tracking the expression of cells, gene therapy, etc.

Figure 1:
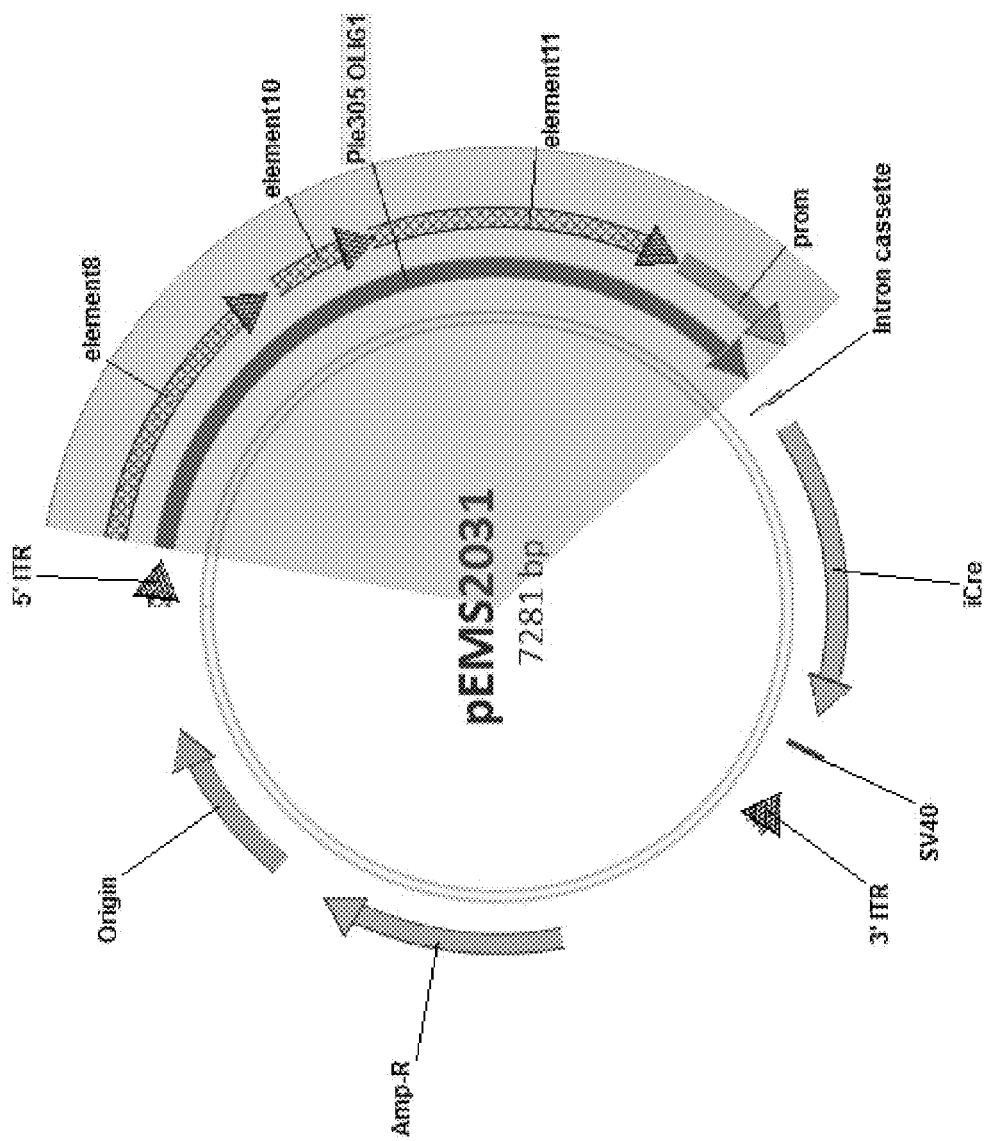

8 Claims, 11 Drawing Sheets
(11 of 11 Drawing Sheet(s) Filed in Color)
Specification includes a Sequence Listing.

OLIG1 MINI-PROMOTERS: PIE305

CROSS REFERENCE

This application claims benefit of U.S. Provisional Patent Application No. 62/501,809, filed May 5, 2017, which application is incorporated herein by reference in its entirety.

FIELD

The invention relates to gene promoters and regulatory elements. More specifically, the invention relates to a novel OLIG1 promoter composition and related methods.

BACKGROUND

The OLIG1 gene encodes the oligodendrocyte lineage transcription factor 1, a basic helix-loop-helix transcription factor (bHLH). OLIG1 is expressed in oligodendrocyte precursors and mature oligodendrocytes (Lu, Yuk et al. 2000; Zhou, Wang et al. 2000; Balasubramaniyan, Timmer et al. 2004; Othman, Frim et al. 2011). These bHLH transcription factors are important in cortical brain development. Some research indicates that OLIG1 may also be expressed in oligodendroglial or other brain tumors (Brena, Morrison et al. 2007; Wu, Richard et al. 2012), and thus an OLIG1-based Mini-Promoter could be used to identify and treat such cells (Hoang-Xuan, Aguirre-Cruz et al. 2002). Furthermore, disorders such as multiple sclerosis wherein there are defects in myelination of neuronal cells, may require the functioning of OLIG1-expressing cells in order to remyelinate axons, implicating the use of an OLIG1 Mini-Promoter in therapeutic contexts (Burton 2005; Goris, Yeo et al. 2006; Arnett, Fancy et al. 2004; Maire, Wegener et al. 2010; Liu, Jiang et al. 2011; Whitman, Blanc et al. 2012). Other evidence implicates OLIG1-dysfunction in neurodevelopmental disorders, such as Down syndrome (Chakrabarti, Best et al. 2010).

There is a need for a characterized human OLIG1 promoter for gene expression, for instance in human gene therapy applications. It is particularly useful to identify small promoter elements that are sufficient to drive expression in regions of the brain, for instance in oligodendrocytes. Such small promoter elements, or "mini-promoters" are particularly useful in certain applications, for instance their compact size make "mini-promoters" more amenable to insertion into space-limited viral vectors used in gene therapy applications.

OLIG1 promoter elements are described in the art, including the promoter known as Ple151 (Portales-Casamar, Swanson et al. 2010). Other OLIG1-based promoters include transcriptional studies of the murine homolog (Olig1) that showed a 289 bp fragment from the promoter region could drive the expression of a reporter gene (Gong, Lin et al. 2008). In addition, a previous study also investigated conserved and non-conserved functional elements in the murine homologs of OLIG1 and OLIG2 and identified a class of conserved enhancer elements located upstream of OLIG2 (Friedli, Barde et al. 2011).

SUMMARY

Novel nucleic acid sequence compositions and methods relating to minimal human OLIG1 promoters are provided. It has surprisingly been found that certain minimal OLIG1 promoter elements alone are sufficient and capable of expressing in specific cell types, including without limitation in cells of the brain.

In one embodiment, there is provided an isolated nucleic acid fragment comprising an OLIG1 mini-promoter, wherein the OLIG1 mini-promoter comprises one or more OLIG1 regulatory elements operably linked in a non-native conformation to an OLIG1 basal promoter. The OLIG1 mini-promoter may have a nucleic acid sequence substantially similar in sequence and function to SEQ ID NO: 1 ("Ple305"). The OLIG1 regulatory elements may have a nucleic acid sequence which is substantially similar in sequence and function to any one, two or all of SEQ ID NO: 3-5. The OLIG1 basal promoter may have a nucleic acid sequence which is substantially similar in sequence and function to SEQ ID NO: 2. The OLIG1 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, cre recombinase, and the like as known in the art. The expressible sequence may encode a protein of interest, for example a therapeutic protein, receptor, antibody, growth factor, cas9, and the like. The expressible sequence may encode an RNA interference molecule, guide RNA, and the like.

In one embodiment, there is provided an expression vector comprising an OLIG1 mini-promoter, wherein the OLIG1 mini-promoter comprises one or more OLIG1 regulatory elements operably linked in a non-native conformation to an OLIG1 basal promoter. The OLIG1 mini-promoter may have a nucleic acid sequence, which is substantially similar in sequence and function to SEQ ID NO: 1 ("Ple305"). The OLIG1 regulatory elements may have a nucleic acid sequence which is substantially similar in sequence and function to any one, two or all of SEQ ID NO: 3-5. The OLIG1 basal promoter may have a nucleic acid sequence, which is substantially similar in sequence and function to SEQ ID NO: 2. The OLIG1 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, cre recombinase, and the like as known in the art. The expressible sequence may encode a protein of interest, for example a therapeutic protein, receptor, antibody, growth factor, cas9, and the like. The expressible sequence may encode an RNA interference molecule, guide RNA, and the like.

In one embodiment, there is provided a method for expressing a gene, protein, RNA interference molecule or the like in a cell, the method comprising introducing into the cell an expression vector comprising an OLIG1 mini-promoter element, wherein the OLIG1 mini-promoter element comprises one or more OLIG1 regulatory elements operably linked in a non-native conformation to an OLIG1 basal promoter element. Cells of interest include, without limitation, cells of the peripheral or central nervous system and progenitors thereof, e.g. embryonic stem cells, neural stem cells, neurons, glial cells, astrocytes, oligodendrocytes etc. The OLIG1 mini-promoter may have a nucleic acid sequence, which is substantially similar in sequence and function to SEQ ID NO: 1 ("Ple305"). The OLIG1 regulatory elements may have a nucleic acid sequence which is substantially similar in sequence and function to any one, two or all of SEQ ID NO: 3-5. The OLIG1 basal promoter may have a nucleic acid sequence, which is substantially similar in sequence and function to SEQ ID NO: 2. The OLIG1 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, cre recombinase, and the like as known in the art. The expressible sequence may encode a protein of interest, for example a therapeutic protein, receptor, antibody, growth factor, cas9, and the like. The expressible sequence may encode an RNA interference molecule, guide RNA, and the like.

In one embodiment, there is provided a method for identifying or labeling a cell, the method comprising introducing into the cell an expression vector comprising an OLIG1 mini-promoter element, wherein the OLIG1 mini-promoter element comprises one or more OLIG1 regulatory elements operably linked in a non-native conformation to an OLIG1 basal promoter element, and wherein the expressible sequence comprises a reporter gene. The OLIG1 mini-promoter element may have a nucleic acid sequence substantially similar in sequence and function to SEQ ID NO: 1 ("Ple305"). The OLIG1 regulatory elements may have a nucleic acid sequence which is substantially similar in sequence and function to any one, two or all of SEQ ID NO: 3-5. The OLIG1 basal promoter element may have a nucleic acid sequence substantially similar in sequence and function to SEQ ID NO: 2. In some embodiments, the cell is a peripheral or central nervous system cell or progenitors thereof, including, without limitation, embryonic stem cells, neural stem cells, glial cells, astrocytes, neurons, oligodendrocytes and the like etc. Reporter gene sequences include, for example luciferase, beta-galactosidase, green fluorescent protein, enhanced green fluorescent protein, cre recombinase, and the like as known in the art. The expressible sequence may encode a protein of interest, for example a therapeutic protein, receptor, antibody, growth factor, cas9, RNA interference molecule, guide RNA, and the like.

In one embodiment, there is provided a method for monitoring or tracking the development or maturation of a cell, the method comprising: 1) introducing into the cell an expression vector comprising an OLIG1 mini-promoter element operably linked to an expressible sequence, wherein the OLIG1 mini-promoter element comprises one or more OLIG1 regulatory elements operably linked in a non-native conformation to an OLIG1 basal promoter element, and wherein the expressible sequence comprises a reporter gene; and 2) detecting the expression of the reporter gene in progeny of the cell as a means of determining the lineage, identity or developmental state of the cell or cell progeny. The OLIG1 mini-promoter element may have a nucleic acid sequence substantially similar in sequence and function to SEQ ID NO: 1 ("Ple305"). The OLIG1 regulatory elements may have a nucleic acid sequence which is substantially similar in sequence and function to any one, two or all of SEQ ID NO: 3-5. The OLIG1 basal promoter element may have a nucleic acid sequence substantially similar in sequence and function to SEQ ID NO: 2. In some embodiments, the cell is a peripheral or central nervous system cell or progenitors thereof, including, without limitation, embryonic stem cells, neural stem cells, glial cells, neurons, astrocytes, oligodendrocytes and the like.

In certain embodiments, there is thus provided a method of treatment of a subject having a disease involving oligodendrocytic cells and the like, the method comprising administering to the subject a therapeutically effective dose of a composition comprising an OLIG1 mini-promoter element, wherein the OLIG1 mini-promoter element comprises one or more OLIG1 regulatory elements operably linked in a non-native conformation to an OLIG1 basal promoter element. The OLIG1 mini-promoter element may have a nucleic acid sequence substantially similar in sequence and function to SEQ ID NO: 1 ("Ple305"). The OLIG1 regulatory elements may have a nucleic acid sequence which is substantially similar in sequence and function to any one, two or all of SEQ ID NO: 3-5. The OLIG1 basal promoter element may have a nucleic acid sequence substantially similar in sequence and function to SEQ ID NO: 2. The disease or condition may include neurodegenerative diseases, such as Alzheimer's disease, dementia, multiple sclerosis, amyotrophic lateral sclerosis, multiple system atrophy, Parkinson's disease; Down's syndrome, and traumatic brain injury. The disease or condition may also include any of which is a result of defective oligodendrocyte cells and the like functioning at the cellular or systems level. The disease or condition may also include tumors.

SHORT DESCRIPTION OF FIGURES

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1—Viral expression vector (pEMS2031) into which OLIG1 promoter elements were inserted into for expression studies. The OLIG1 promoter with a nucleic acid sequence corresponding to SEQ ID NO: 1 (Ple305) was inserted into the multiple cloning site (MCS) of the backbone vector such that it became operably linked to the icre reporter gene.

Figure 2:
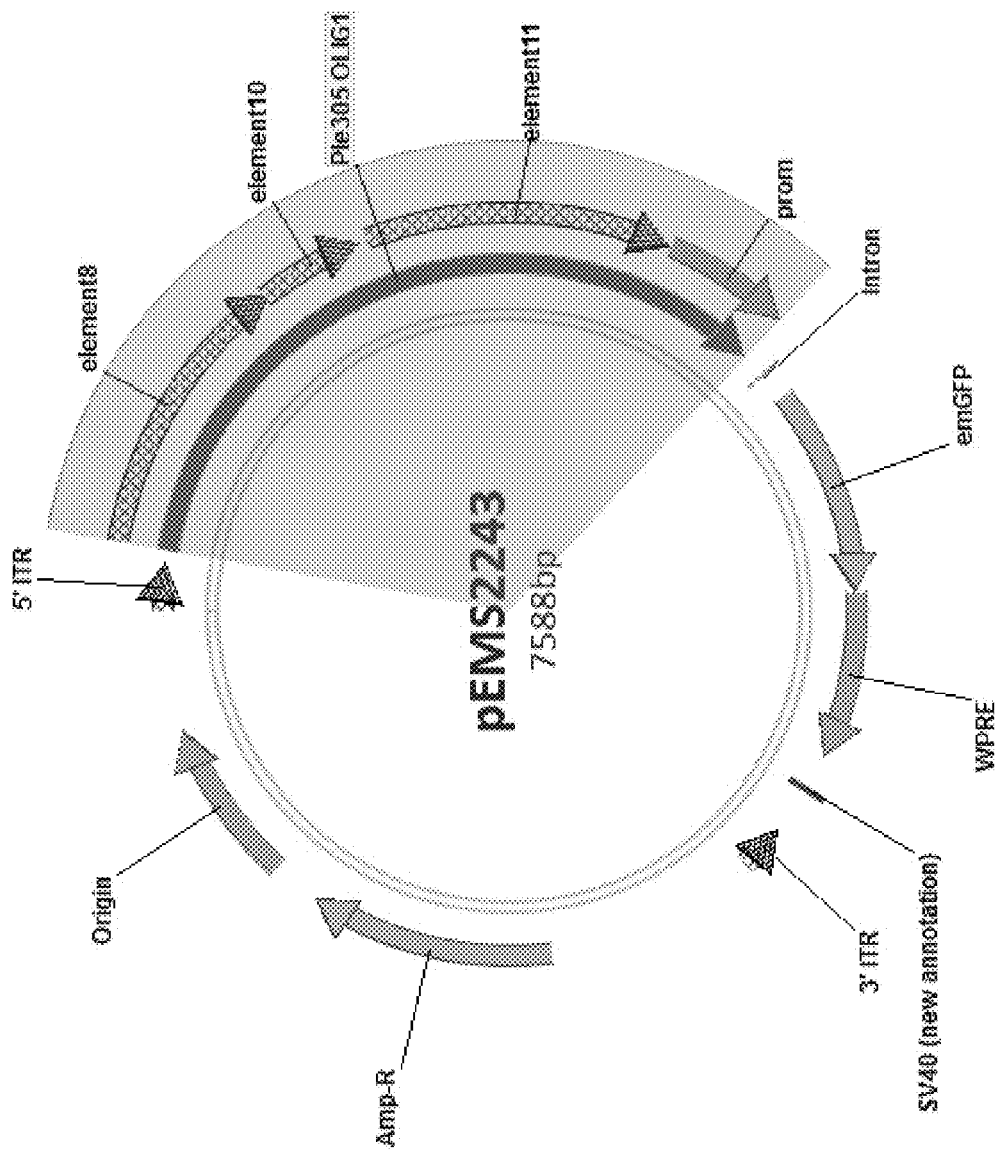

FIG. 2—Viral expression vector (pEMS2243) into which OLIG1 promoter elements were inserted into for expression studies. The OLIG1 promoter with a nucleic acid sequence corresponding to SEQ ID NO: 1 (Ple305) was inserted into the multiple cloning site (MCS) of the backbone vector such that it became operably linked to the EmGFP (emerald green fluorescent protein) reporter gene.

Figure 3:
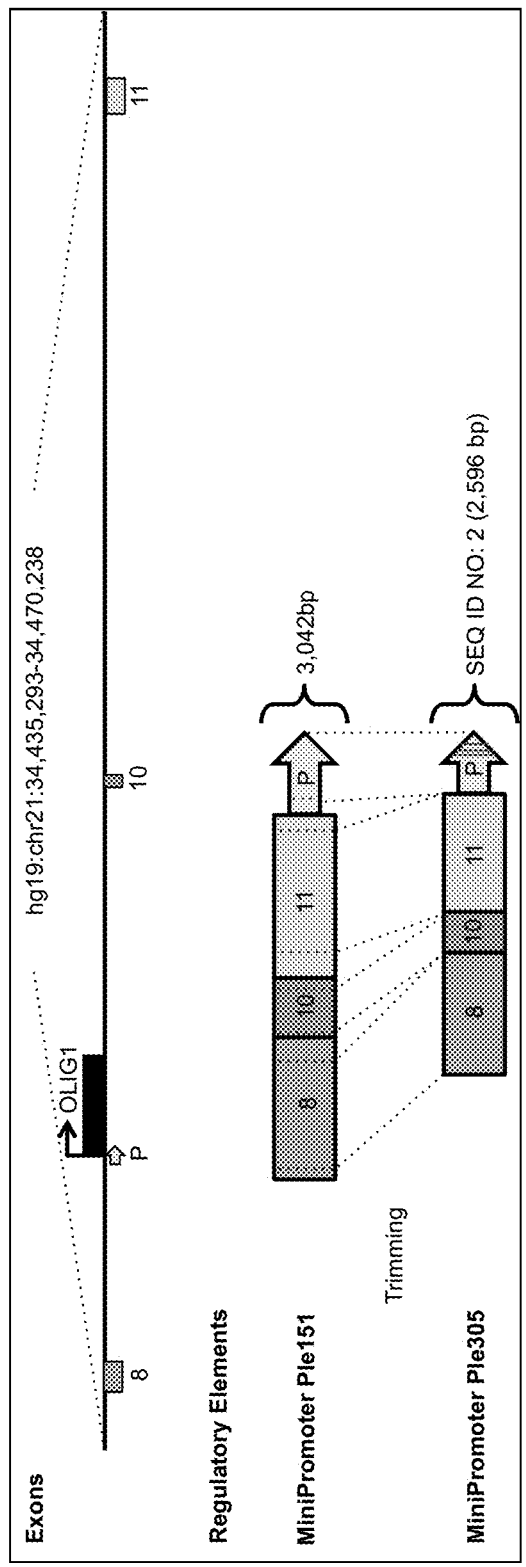

FIG. 3—Overview of the human OLIG1-based Mini-Promoters Ple151 (included as SEQ ID NO:6) and Ple305 (SEQ ID NO: 1). Ple305 comprises the OLIG1 regulatory elements 8, 10, 11 (coloured boxes; SEQ ID NO: 3, 4 and 5 respectively) linked in a non-native conformation to the OLIG1 basal promoter element (P; red arrow; SEQ ID NO: 4). Ple305 is 15% shorter than Ple151. Its elements (SEQ ID NO: 3-5) are trimmed versions of the Ple151 elements, as indicated by dotted lines. The basal promoter contains nucleotide substitutions (red line) designed to improve transcription factor binding.

Figure 4:
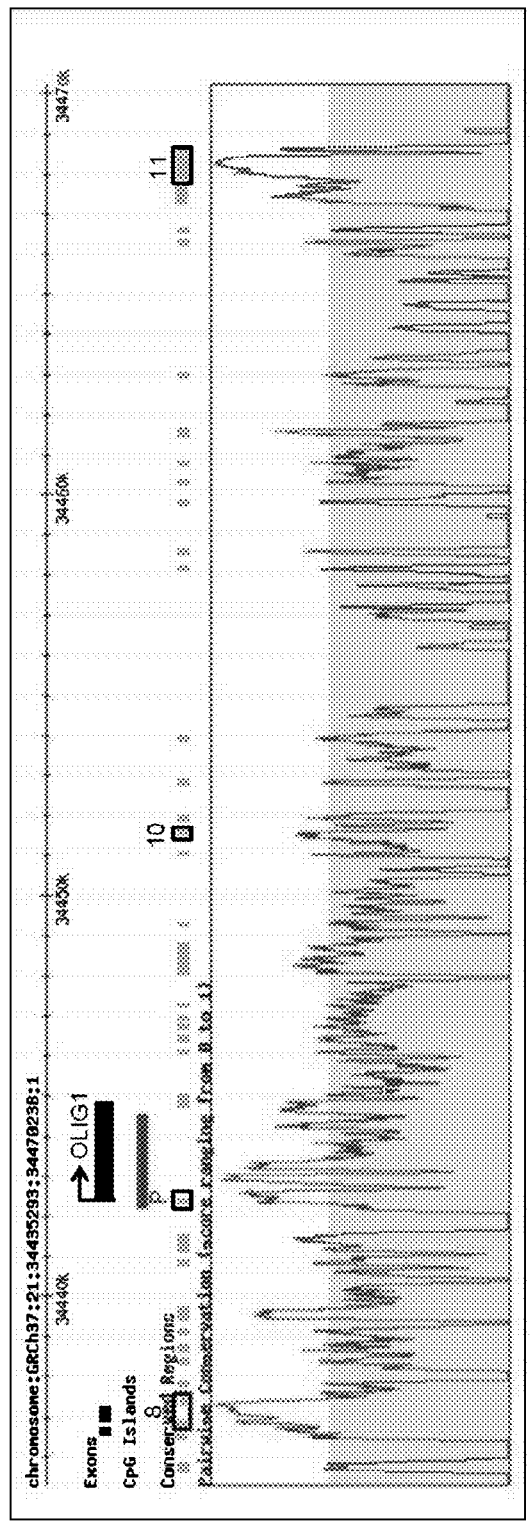

FIG. 4—Conservation profile of the human OLIG1-based Mini-Promoter Ple305 (SEQ ID NO: 2). "Conserved Regions" (cyan) are determined by alignment of the human sequence (chr21:34,435,293-34,470,238, genome assembly hg19) and its mouse homolog (chr16:91,262,240-91,293, 688, genome assembly mm9) using a threshold on the percentage of identity of 61% (see shading in "Pairwise Conservation" box). Black squares delimit the Mini-Promoter regulatory element 8, 10 and 11 (SEQ ID NO: 3, 4 and 5 respectively) and basal promoter element (P; SEQ ID NO: 2). The red line indicates the "Pairwise Conservation" score at each position. Overall, about 61.7% of the Mini-Promoter sequence is conserved between human and mouse.

Figure 5:
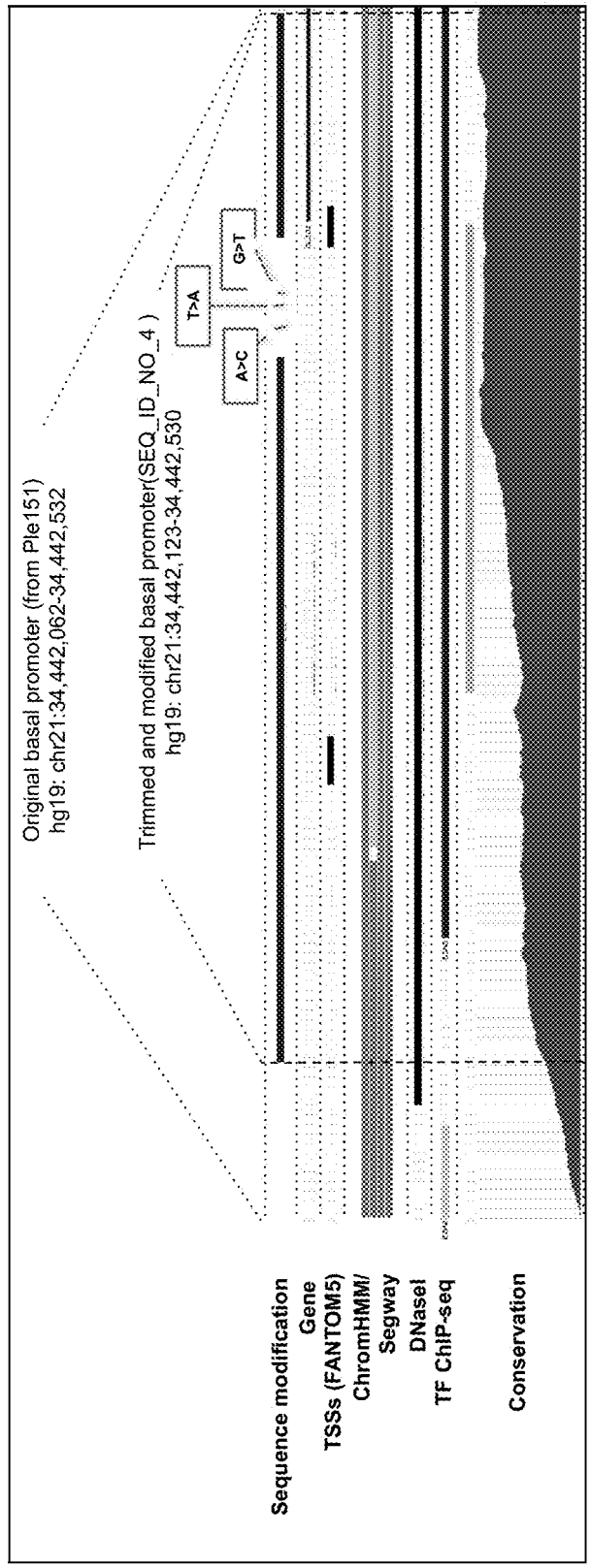

FIG. 5—Supporting evidence for the design of basal promoter (SEQ ID NO: 2). The original basal promoter was of Ple151 (SEQ ID NO: 6) was trimmed at both ends (dotted lines) based on conservation between human and mouse ("Conservation" red profile). The trimmed promoter maintains 87% of the nucleotides from the original Ple151 promoter (dotted lines), except for 3 nucleotide substitutions designed to improve transcription factor (TF) binding in the trimmed promoter (red boxes). About 45% of the trimmed promoter is conserved between human and mouse ("Conservation"; cyan thick lines and red profile). The trimmed promoter is open ("DNase I" black thick line) and predicted to be an active enhancer by combined "ChromHMM/Segway" (yellow thick line). It contains two FANTOM5 transcription start sites (TSS; black lines) and several "TF ChIP-seq" peaks (gray thick lines).

Figure 6:
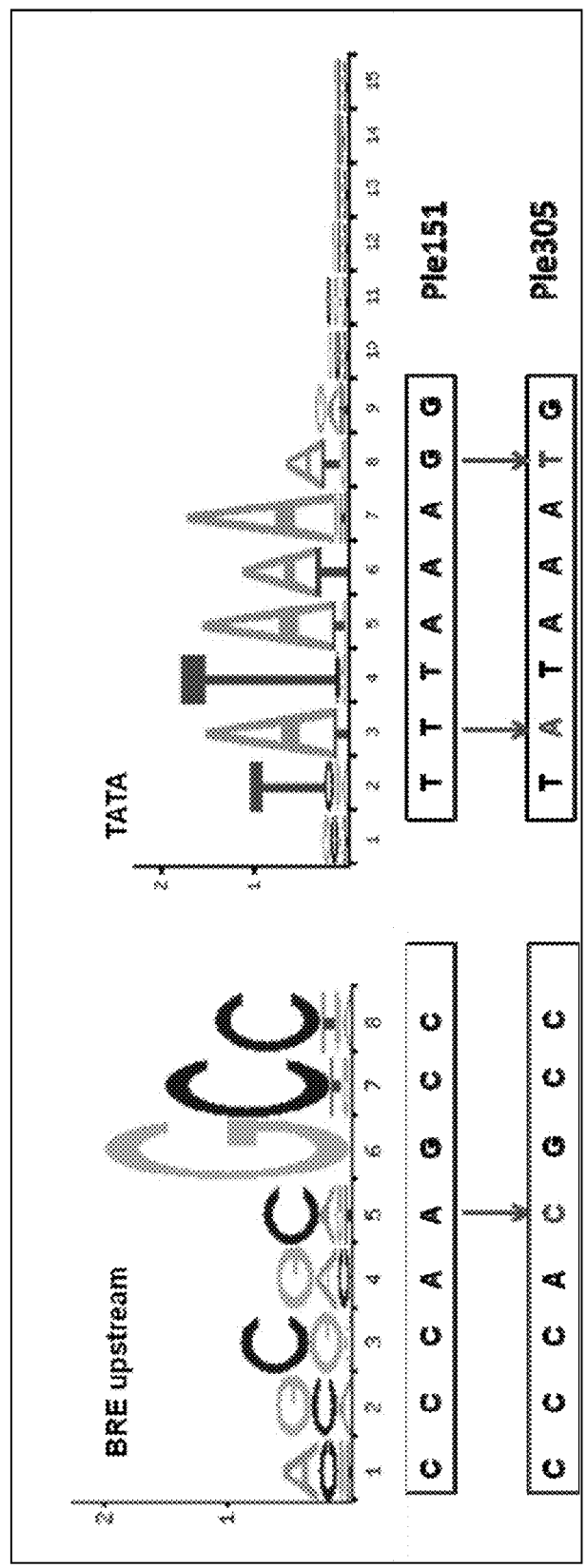

FIG. 6—Nucleotide modifications introduced in the basal promoter (SEQ ID NO: 2). The B recognition element (BRE) and TATA box are DNA sequences found in the core promoter region of most genes in eukaryotes (sequence logos). These sequences are recognized by the transcription factors TFIIB and TBP, respectively. The BRE and TATA sequences from the OLIG1-base Mini-Promoters Ple151 (SEQ ID NO: 6) and Ple305 (SEQ ID NO:1) are shown for comparison. In Ple305, three nucleotide substitutions (red nucleotides) are designed for optimizing the BRE and TATA sequences and improve the binding of TFIIB and TBP to these sites.

Figure 7:
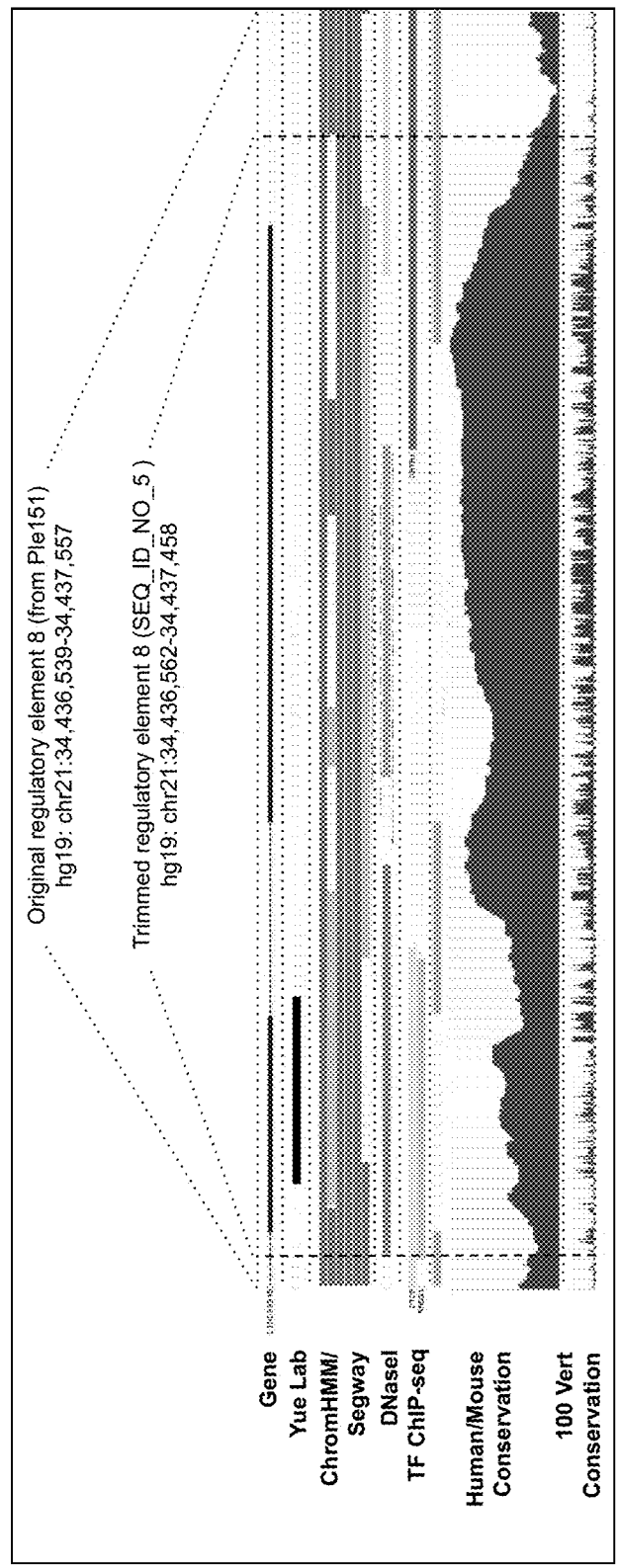

FIG. 7—Supporting evidence for the design of regulatory element 8 (SEQ ID NO: 3). The original regulatory element 8 from Ple151 (SEQ ID NO: 6) was trimmed at both ends (dotted lines) based on conservation between human and mouse and across 100 vertebrates ("Human/Mouse" and "100 Vert" conservation profiles). The trimmed region maintains 88% of the nucleotides from the original Ple151 region (dotted lines). About 38% of the trimmed region is conserved between human and mouse ("Conservation"; cyan thick lines and red profile). The trimmed region is open ("DNase I" and "Yue Lab" gray/black thick lines) and predicted to be an active enhancer by a combined hidden Markov model-based method for the functional segmentation of genomes ("ChromHMM/Segway"; yellow thick line). It is bound by several transcription factors (TFs), as identified by chromatin immunoprecipitation (ChIP) coupled to massively parallel DNA sequencing (ChIP-seq), which allows for the identification of protein-DNA interactions in vivo (gray thick lines).

Figure 8:
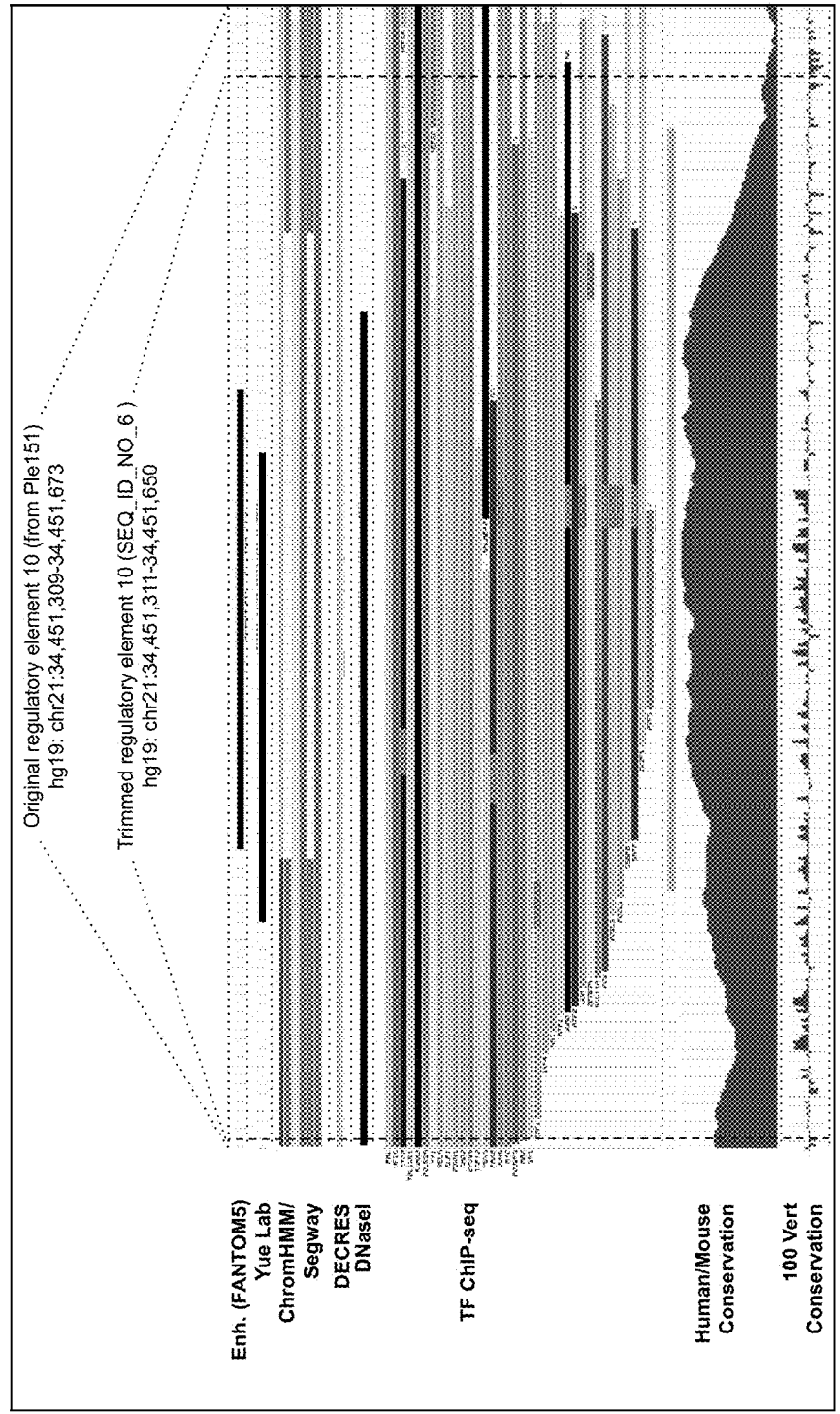

FIG. 8—Supporting evidence for the design of regulatory element 10 (SEQ ID NO: 4). The original regulatory element 10 contained within Ple151 (SEQ ID NO: 6) was trimmed at both ends (dotted lines) based on conservation between human and mouse and across 100 vertebrates ("Human/Mouse" and "100 Vert" conservation profiles). The trimmed region maintains 93% of the nucleotides from the original Ple151 region (dotted lines). About 72% of the trimmed region is conserved between human and mouse ("Conservation"; cyan thick lines and red profile). The trimmed region is an enhancer as defined in the FANTOM5 project by cap analysis of gene expression (CAGE) (black lines). It is predicted to be an active enhancer/promoter by combined "ChromHMM/Segway" (red/yellow thick lines), and a supervised deep learning method that identifies enhancer and promoter regions in the human genome ("DECRES"; yellow thick line). The trimmed region is open ("DNase I" and "Yue Lab" black/gray thick lines) and is enriched in "TF ChIP-seq" peaks (black/gray thick lines).

Figure 9:
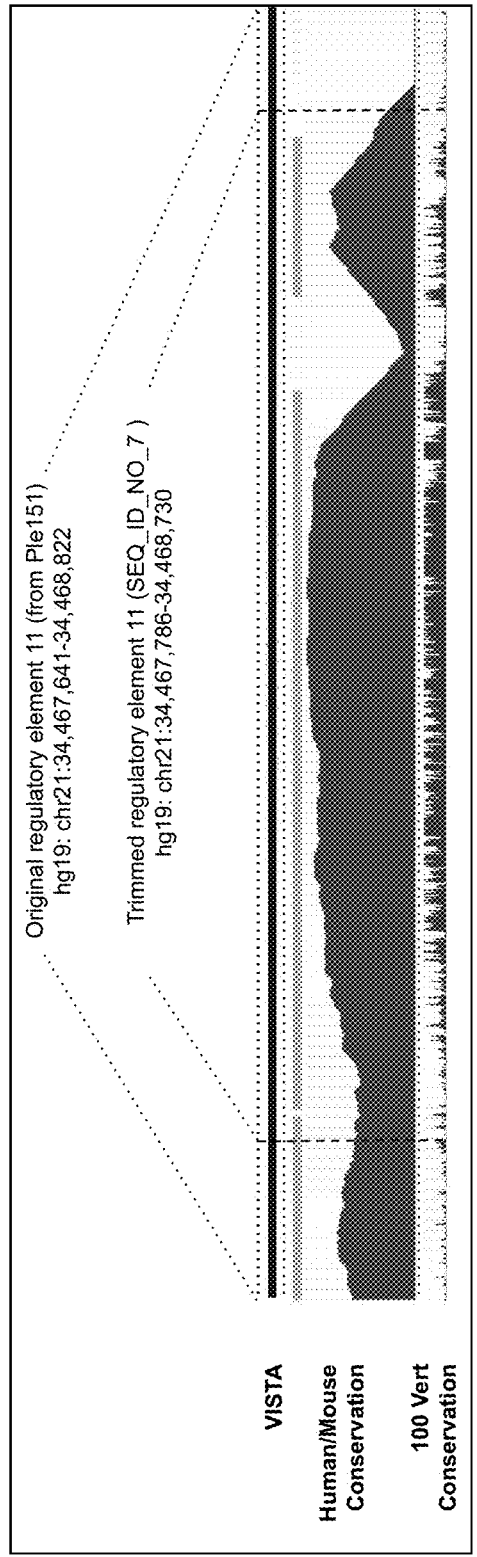

FIG. 9—Supporting evidence for the design of regulatory element 11 (SEQ ID NO: 5). The original regulatory element 11 contained within Ple151 (SEQ ID NO: 6) was trimmed at both ends (dotted lines) based on conservation between human and mouse and across 100 vertebrates ("Human/Mouse" and "100 Vert" conservation profiles). The trimmed region maintains 80% of the nucleotides from the original Ple151 region (dotted lines). About 88% of the region is conserved between human and mouse ("Conservation"; cyan thick lines and red profile). The region overlaps with a VISTA enhancer (black line), which was validated experimentally in mice using a transgenesis enhancer assay.

Figure 10:
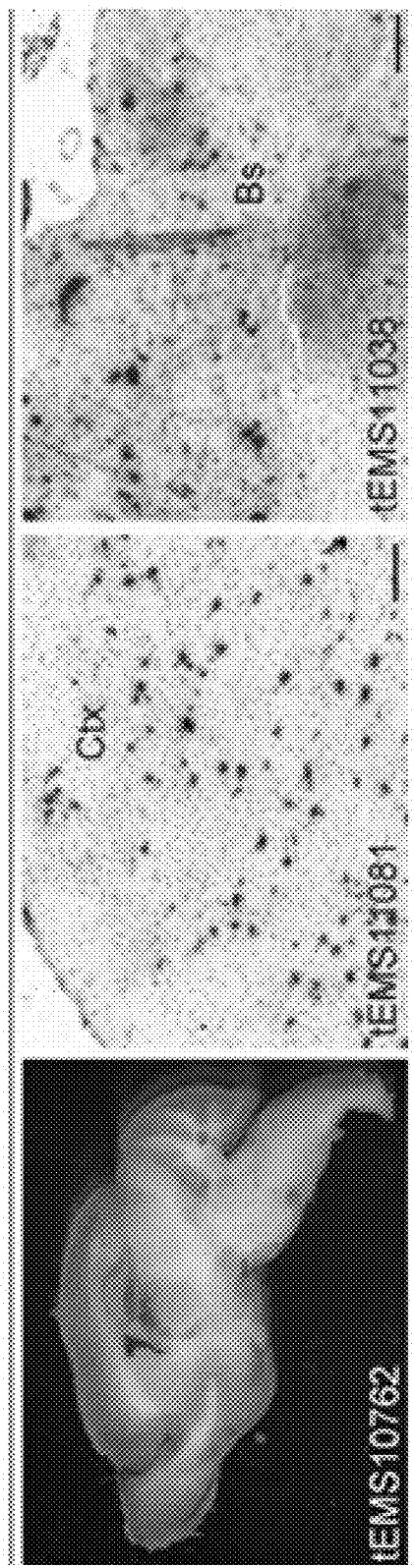

FIG. 10—Ple305 expresses in oligodendroglia of the brain. The Ple305 Mini-Promoter driving icre expression was constructed and ssAAV9 virus generated (vEMS52). P0 mice were injected intravenously with virions and mice were harvested at P21 and P56, perfused, and stained overnight for lacZ activity (blue), reporting on promoter activity, with neutral red counterstain. A sagittal 1 mm section of the brain demonstrates light staining throughout many brain regions (first image). Cryosections reveal cells with puffy processes indicative of oligodendrocytes in the cortex (second image), and brainstem (third image). Bs, brainstem; Ctx, cortex; icre, improved cre recombinase; RR, regulatory regions, ssAAV9, single-stranded adeno-associated virus 9; tEMS, brain tissue number indicating different animals. Scale bars are 100 μm.

Figure 11:

FIG. 11—Ple305 expresses in oligodendroglia of the brain. The Ple305 Mini-Promoter driving EmGFP expression was constructed and ssAAV9 virus generated (vEMS144). P4 mice were injected intravenously with virions and mice were harvested at P32, perfused, and antibody used to detect EmGFP (green), reporting on promoter activity, with DAPI counterstain (blue). A sagittal section of the brain demonstrates staining throughout many brain regions (first image). Cryosections reveal cells with puffy processes indicative of oligodendrocytes in the cortex (second image), spinal cord (third image), and dorsal root ganglion (fourth image). Ctx, cortex; EmGFP, emerald green fluorescent protein; RR, regulatory regions, ssAAV9, single-stranded adeno-associated virus 9.

DETAILED DESCRIPTION

The compositions provided herein include novel polynucleotides comprising OLIG1 promoter elements (also referred to herein as OLIG1 mini-promoters) as well as novel expression vectors comprising said OLIG1 promoter elements (or mini-promoters). Also provided are various methods utilizing these novel OLIG1 promoter (or mini-promoter) elements or expression vectors.

The term 'OLIG1' refers to the gene that encodes the oligodendrocyte lineage transcription factor 1, other aliases include class B Basic Helix-loop-helix protein 6 (BHLHB6) and Class E Basic Helix-loop-helix protein 21 (BHLHE21). The human homolog of OLIG1 is encoded by the human gene identified as EntrezGene #116448 and is located on chromosome 21 at location 21q22.11. The protein encoded by human OLIG1 has the Protein Accession NP_620450.2 however other protein accession numbers may also be assigned to this protein. OLIG1 may also include other isoforms and/or splice variants. Other mammalian OLIG1 homologs may include but are not limited to: *Rattus norvegicus* (EntrezGene #60394), *Mus musculus* (EntrezGene #50914), *Pan troglodytes* (EntrezGene #706574) and *Macaca mulatta* (EntrezGene #706574).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'OLIG1 basal promoter', in the context as used herein, is a nucleic acid compound having a sequence with at least 65%, at least 70%, at least 80%, at least 85%, at least 90%, at least 95%, or at least 99% similarity to SEQ ID NO: 2.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. An 'OLIG1 regulatory element', in the context as used herein, is a nucleic acid compound having a sequence with at least 65%, at least 70%, at least 80%, at least 85%, at least 90%, at least 95%, or at least 99% similarity to one, two or all of SEQ ID NOs: 3-5. In certain embodiments as described herein, different promoters of the OLIG1 gene are provided. In some embodiments, the OLIG1 promoter comprises one or more OLIG1 regulatory elements operably linked to an OLIG1 basal promoter.

The term 'operably linked', in the context as used herein means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters are apparent to one of skill in the art. In some embodiments of the invention, there are thus provided novel OLIG1 mini-promoters comprising one or more OLIG1 regulatory elements operably linked in a non-native conformation to an OLIG1 basal promoter. In general, the spacing between the OLIG1 regulatory element and the OLIG1 basal promoter is not more than about 15 KB, generally not more than about 10 kb, usually not more than about 1 kb, more often not more than about 500 nt, and may be not more than about 100 nt, down to a direct joining of the two sequences.

In some embodiments an OLIG1 minipromoter is a nucleic acid compound having a sequence with at least 65%, at least 70%, at least 80%, at least 85%, at least 90%, at least 95%, or at least 99% similarity to SEQ ID NO:1. In some such embodiments, the OLIG1 minipromoter sequence is identical to SEQ ID NO:1 at the conserved regions indicated in Table 1, i.e. SEQ ID NO:1 nt. 1-22; 196-349; 731-897; 979-1223; 1239-1263; 1269-1928; 2014-2160; and 2334-2516, but may vary at outside of the conserved regions, providing for an overall sequence identify of up to at least 65%, at least 70%, at least 80%, at least 85%, at least 90%, at least 95%, or at least 99% to SEQ ID NO:1.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art. In some embodiments of the invention, the expression sequence may include genome editing proteins such as zinc finger nucleases (ZFNs), transcription activator-like effector nucleases (TALENs) or clustered regularly interspaced short palindromic repeats enzymes (CRISPRs), or encode guide RNAs for such purposes.

The term 'RNA' as used herein includes full-length RNA molecules, which may be coding or non-coding sequences, fragments, and derivatives thereof. For example, a full-length RNA may initially encompass up to about 20 kb or more of sequence, and frequently will be processed by splicing to generate a small mature RNA. Fragments, RNAi, miRNA, anti-sense molecules, and guide RNAs may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3'-5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements in a fashion that does not significantly alter transcriptional activity, as described above, results in sequences with 'substantial sequence similarity' to the original sequence, i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by northern blot assay or reverse transcriptase PCR of mRNA expression, western blot or ELISA assay of protein expression, immunoprecipitation assay of protein expression, a functional assay, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, adeno-associated virus and the like; etc. Many such vectors have been described in the art and are suitable for use with the promoters described herein. Expression vectors include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

Introduction of nucleic acids or expression vectors into cells may be accomplished using techniques well known in the art, for example microinjection, electroporation, particle bombardment, viral delivery, or chemical transformation, such as calcium-mediated or lipid-mediated transformation, as described for example in Maniatis et al. 1982, Molecular Cloning, A laboratory Manual, Cold Spring Harbor Laboratory or in Ausubel et al. 1994, Current protocols in molecular biology, John Wiley and Sons.

In certain embodiments of the invention, there are provided methods of treatment using the nucleic acids or expression vectors disclosed herein, for instance for gene therapy applications. The nucleic acids or expression vectors disclosed herein may be administered in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit, monkey or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, intraparenchymal, subcutaneous, intrathecal, intraocular, topical, or oral administration. An excipient may include sterile aqueous solutions or dispersions for extemporaneous preparation of sterile injectable solutions or dispersion. Use of such media for preparation of medicaments is known in the art.

The nucleic acids or expression vectors disclosed herein may be administered to a subject using a viral delivery system. For instance, the nucleic acids may be inserted into a viral vector using well known recombinant techniques. The subsequent viral vector may then be packaged into a virus, such as adenovirus, lentivirus, retrovirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenous, inhalation, intramuscular, intraparenchymal, subcutaneous, topical, intraperitoneal, intra-ocular, intra-rectal or intra-vaginal suppository, sublingual, and the like. The compounds disclosed herein may be administered as a sterile aqueous solution, or may be administered in a fat-soluble excipient, or in another solution, suspension, patch, tablet or paste format as is appropriate. A composition comprising the compounds may be formulated for administration by inhalation. For instance, a compound may be combined with an excipient to allow dispersion in an aerosol. Examples of inhalation formulations will be known to those skilled in the art. Other agents may be included in combination with the compounds disclosed herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

OLIG1 Mini-Promoter

Disclosed herein are novel OLIG1 mini-promoter sequences which are capable of effecting transcriptional expression in a spatial and temporal fashion in the brain and related tissues. Certain OLIG1 mini-promoters of the invention comprise minimal OLIG1 promoter and regulatory elements joined in a non-native configuration, thus providing advantageous characteristics. Also provided are novel expression vector compositions comprising OLIG1 mini-promoters, which allow consistent specific spatiotemporal transcription of expression sequences. Also provided are novel methods utilizing these OLIG1 mini-promoters and expression vectors.

The OLIG1 promoters of the invention, as described herein, are referred to as 'mini-promoters' to reflect the fact that the mini-promoters comprise minimal OLIG1 promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance a human OLIG1 regulatory element corresponding to SEQ ID NO: 5 and the human OLIG1 basal promoter elements corresponding to SEQ ID NO: 2 or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Examples, that the human OLIG1 mini-promoter having a sequence corresponding to SEQ ID NO: 1 (referred to in the Working Examples as Ple305), and which is comprised of human OLIG1 regulatory elements (SEQ ID NO: 3-5) operably linked in a non-native conformation to human OLIG1 basal promoters (SEQ ID NO: 2), is capable of directing expression of an expressible sequence which is operably linked downstream of the OLIG1 promoter in specific cell types in different regions of the brain. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters as disclosed herein may be modified with respect to the native regulatory and/or native basal promoter sequence. In general, such modifications will not change the functional activity of the promoter with respect to cell-type selectivity; and to the rate of transcription in cells where the promoter is active. The modified promoters provide for a transcription rate of an expressible sequence operably linked to a modified promoter sequence that is at least about 75% the transcription rate of the promoter sequence of SEQ ID NO: 1 ("Ple305"), at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 2-5 that are not conserved may be deleted or substituted, usually modifications that retain the spacing between conserved sequences is preferred. In general, the spacing between the regulatory element and the basal promoter is not more than about 10 kb, generally not more than about 1 kb, usually not more than about 500 nt, and may be not more than about 100 nt, down to a direct joining of the two sequences.

In one embodiment of the invention, there is provided an isolated nucleic acid fragment comprising an OLIG1 mini-promoter, wherein the OLIG1 mini-promoter comprises an OLIG1 regulatory element operably linked in a non-native conformation to an OLIG1 basal promoter. The OLIG1 mini-promoter may have a nucleic acid sequence which is substantially similar in sequence and function to SEQ ID NO: 1 ("Ple305"). The OLIG1 basal promoter may have a nucleic acid sequence which is substantially similar in sequence and function to SEQ ID NO: 2. The OLIG1 regulatory elements may have a nucleic acid sequence which is substantially similar in sequence and function to SEQ ID NO: 3-5. The OLIG1 mini-promoters may further be operably linked to an expressible sequence, e.g. reporter genes, genes encoding a polypeptide of interest, guide RNA, and regulatory RNA sequences such as miRNA, siRNA, antisense RNA, etc., and the like. Reporter gene sequences include, for example luciferase, beta-galactosidase, green fluorescent protein, enhanced green fluorescent protein, cre recombinase, and the like as known in the art. The expressible sequence may encode a protein of interest, for example a therapeutic protein, receptor, antibody, growth factor, cas9, and the like. The expressible sequence may encode an RNA interference molecule.

It is an object to provide means of expressing a gene, protein, RNA interference molecule or the like in a cell, tissue or organ. As such, the inventors thus provide novel expression vectors comprising an OLIG1 mini-promoter which are capable of accomplishing this task. In one embodiment, there is provided an expression vector comprising an OLIG1 mini-promoter, wherein the OLIG1 mini-promoter comprises one or more OLIG1 regulatory elements operably linked in a non-native conformation to an OLIG1 basal promoter. The OLIG1 mini-promoter may have a nucleic acid sequence which is substantially similar in sequence and function to SEQ ID NO:1 ("Ple305"). The OLIG1 basal promoter may have a nucleic acid sequence which is substantially similar in sequence and function to SEQ ID NO: 2. The OLIG1 regulatory elements may have a nucleic acid sequence which is substantially similar in sequence and function to SEQ ID NO: 3-5. The OLIG1 mini-promoter may further be operably linked to an expressible sequence, e.g. reporter genes, genes encoding a polypeptide of interest, guide RNA, and regulatory RNA sequences such as miRNA, siRNA, anti-sense RNA, etc., and the like. Reporter gene sequences include, for example luciferase, beta-galactosidase, green fluorescent protein, cre recombinase, enhanced green fluorescent protein, and the like as known in the art. The expressible sequence may encode a protein of interest, for example a therapeutic protein, receptor, antibody, growth factor, cas9, and the like. The expressible sequence may encode an RNA interference molecule.

The inventors have herein demonstrated that expression vectors comprising novel OLIG1 mini-promoter elements are capable of directing transcription of an expression sequence in specific cell types, for instance in oligodendrocytes in the brain. In one embodiment of the invention, there is thus provided a method for expressing a gene, protein, RNA interference molecule or the like in a cell, the method comprising introducing into the cell an expression vector comprising an OLIG1 mini-promoter element, wherein the OLIG1 mini-promoter element comprises one or more OLIG1 regulatory elements operably linked in a non-native conformation to an OLIG1 basal promoter element. In another embodiment, the OLIG1 mini-promoter comprises an OLIG1 basal promoter. Cells of interest include, without limitation, cells of the peripheral or central nervous system and progenitors thereof, e.g. embryonic stem cells, neural stem cells, neurons, glial cells, astrocytes, oligodendrocytes etc. The OLIG1 mini-promoter may have a nucleic acid sequence which is substantially similar in sequence and function to SEQ ID NO: 1 ("Ple305"). The OLIG1 regulatory elements may have a nucleic acid sequence which is substantially similar in sequence and function to SEQ ID NO: 3-5. The OLIG1 basal promoter may have a nucleic acid sequence which is substantially similar in sequence and function to SEQ ID NO: 2. The OLIG1 mini-promoter may further be operably linked to an expressible sequence, e.g. reporter genes, genes encoding a polypeptide of interest, guide RNA, regulatory RNA sequences such as miRNA, siRNA, anti-sense RNA, etc., and the like. Reporter gene sequences include, for example luciferase, beta-galactosidase, green fluorescent protein, enhanced green fluorescent protein, cre recombinase, and the like as known in the art. The expressible sequence may encode a protein of interest, for example a therapeutic protein, receptor, antibody, growth factor, cas9, and the like. The expressible sequence may encode an RNA interference molecule.

In one embodiment of the invention, there is provided a method for identifying or labeling a cell, the method comprising introducing into the cell an expression vector comprising an OLIG1 mini-promoter element, wherein the OLIG1 mini-promoter element comprises one or more OLIG1 regulatory elements operably linked in a non-native conformation to an OLIG1 basal promoter element, and wherein the expressible sequence comprises a reporter gene. The OLIG1 mini-promoter element may have a nucleic acid sequence substantially similar in sequence and function to SEQ ID NO: 1 ("Ple305"). The OLIG1 regulatory element may have a nucleic acid sequence substantially similar in sequence and function to SEQ ID NO: 3-5. The OLIG1 basal promoter element may have a nucleic acid sequence substantially similar in sequence and function to SEQ ID NO: 2. The inventors have demonstrated that expression vectors comprising certain human OLIG1 promoter elements are capable of expression in specific regions of the brain. In some embodiments, the cell is a peripheral or central nervous system cell or progenitors thereof, including, without limitation, embryonic stem cells, neural stem cells, neurons, glial cells, astrocytes, oligodendrocytes and the like. Reporter gene sequences include, for example luciferase, beta-galactosidase, green fluorescent protein, enhanced green fluorescent protein, cre recombinase, and the like as known in the art. The expressible sequence may encode a protein of interest, for example a therapeutic protein, receptor, antibody, growth factor, cas9, guide RNA, RNA interference molecule and the like.

In further embodiments of the invention, there is provided a method for monitoring or tracking the development or maturation of a cell, the method comprising: 1) introducing into the cell an expression vector comprising an OLIG1 mini-promoter element operably linked to an expressible sequence, wherein the OLIG1 mini-promoter element comprises an OLIG1 regulatory element operably linked in a non-native conformation to an OLIG1 basal promoter element, and wherein the expressible sequence comprises a reporter gene; and 2) detecting the expression of the reporter gene in the cell of in progeny of the cell as a means of determining the lineage, identity or developmental state of the cell or cell progeny. The OLIG1 mini-promoter element may have a nucleic acid sequence substantially similar in sequence and function to SEQ ID NO: 1 ("Ple305"). The OLIG1 regulatory elements may have a nucleic acid sequence substantially similar in sequence and function to SEQ ID NO: 3-5. The OLIG1 basal promoter element may have a nucleic acid sequence substantially similar in sequence and function to SEQ ID NO: 2. In such a fashion, one may be able to follow the development of a parent cell as it differentiates into more mature cells. As an example, one could introduce an expression vector comprising the aforementioned OLIG1 mini-promoter elements into a pluripotent stem cell, monitor the expression of the reporter gene that is being expressed by the OLIG1 promoter elements during the maturation and differentiation of the stem cell and thus determine the state of maturation, for instance in the differentiation of the pluripotent stem cell into a specific brain cell type. The inventors have demonstrated that the OLIG1 mini-promoter elements described herein direct transcriptional expression in certain brain cell types and related tissues, and so detection of reporter gene expression in a cell would thus be indicative of the cellular identity of the cell as being a certain type of brain cell or related cells.

The inventors have herein demonstrated that certain OLIG1 mini-promoter elements disclosed herein are capable of driving expression in the oligodendrocytic cells of the cortex brainstem, spinal cord, and dorsal root ganglion. For instance, it may be desirable to utilize the OLIG1 mini-promoters in a gene therapy or cell therapy application wherein the OLIG1 mini-promoters are utilized to drive expression of a therapeutic or beneficial compound, such as a protein, in oligodendrocytes. In such a way, the therapeutic or beneficial compound may be useful for a disease or condition that involves such cells, involves expression of a therapeutic molecule in the cortex, or which may be improved by expression of the therapeutic or beneficial compound in those cells or other supporting cells in the central nervous system. In certain embodiments of the invention, there is thus provided a method of treatment of a subject having a disease involving oligodendrocyte cells, the method comprising administering to the subject a therapeutically effective dose of a composition comprising an OLIG1 mini-promoter element, wherein the OLIG1 mini-promoter element comprises an OLIG1 regulatory element operably linked in a non-native conformation to an OLIG1 basal promoter element. The OLIG1 mini-promoter element may have a nucleic acid sequence substantially similar in sequence and function to SEQ ID NO: 1 ("Ple305"). The OLIG1 regulatory elements may have a nucleic acid sequence substantially similar in sequence and function to SEQ ID NO: 3-5. The OLIG1 basal promoter element may have a nucleic acid sequence substantially similar in sequence and function to SEQ ID NO: 2. The disease or condition may include neurodegenerative diseases, such as Alzheimer's disease, dementia, multiple sclerosis, amyotrophic lateral sclerosis, multiple system atrophy, Parkinson's disease, Down's syndrome, and traumatic brain injury. The disease or condition may also include any of which is a result of defective oligodendrocyte functioning at the cellular or systems level. The disease or condition may also include tumors.

The inventors herein further describe OLIG1 mini-promoters by way of the following non-limiting examples:

WORKING EXAMPLES

Virus Generation and Analysis

Virus production. The Ple305 Mini-Promoter was generated by direct synthesis by DNA2.0 (Menlo Park, Calif., USA) (SEQ ID NO:1). The Ple305 construct was tested in ssAAV9 (recombinant single-stranded adeno-associated virus) driving either the icre (cre recombinase) reporter, resulting in vEMS52, or the EmGFP (emerald green fluorescent protein) reporter, resulting in vEMS144.

Virus injection. B6-Gt(ROSA26)$^{tm1Sor}$ females were crossed to 129-Gt(ROSA26)$^{tm1Sor}$ to yield hybrid F1 homozygous pups for injecting virus. Plug checks were performed on the females such that the day of birth could be accurately estimated. A standard injection into the superficial temporal vein of a newborn pup was performed using $1 \times 10^{13}$ GC/mL (genome copies per milliliter) virus in a total volume of 50 µL (in PBS) with a 30-gauge needle and a 1 cc syringe. After injections, pups were tattooed for identification and returned to their cage. Mice were injected intravenously with virus at post-natal day 0 (P0) or P4 (method of (Foust et al. 2009)). For the icre reporter, Expression was analyzed at P21 and P56 via recombination of the reporter locus Gt(ROSA26)Sor$^{tmSor1}$ (Soriano 1999). Once recombined, this locus expresses the β-galactosidase (lacZ gene) enzyme. Mice were harvested by cardiac perfusion, sectioned, and stained with the X-gal substrate, which leaves a blue product after enzymatic cleavage by beta-galactosidase. For the EmGFP reporter, expression was analyzed at P32 in wild-type mice. Mice were harvested by cardiac perfusion, sectioned, and the GFP epifluence enhanced with antibody detection.

Harvesting of animals. Virus-injected mice were harvested at P21, P32, or P56 (post-natal day 21 or 56). Animals were given a lethal dose of avertin injected intraperitoneally. Thereafter perfusion with 1×PBS for 2 minutes and 4% PFA/PBS for 8 minutes was performed. Tissues were harvested and post-fixed for 1 hour at 4° C. The tissues were then stored in 0.02% azide/PBS at 4° C.

Histology. Tissues were cryoprotected in 30% sucrose/PBS overnight at 4° C. After embedment in OCT the following day, 20 µm cryosections were directly mounted onto slides. For X-gal staining, tissues were rinsed in PBS and Triton-X/PBS and stained in 0.1% X-gal solution overnight at 30-35° C. After staining sections were rinsed and counterstained with neutral red, dehydrated and mounted with coverslips. X-gal stains blue any cells that have recombined the Gt(ROSA26)$^{tm1Sor}$ locus due to icre recombinase activity and thus expressing the β-galactosidase protein. For EmGFP detection, tissues were signal amplified using a chicken α-GFP antibody (Ayes Labs Inc.; 1:500) and Alexa Fluor 488 secondary (Life Technologies; 1:1000).

Example 1—Design of Ple305 Mini-Promoters

The inventors previously described the design and testing of the Ple151 mini-promoter (as shown in FIG. 3), which is 3,042 nucleotides in length as described in U.S. Pat. No. 8,629,261 (Portales-Casamar, Swanson et al. 2010). Bioinformatically-driven efforts were made to reduce the overall nucleotide length of the mini-promoter to increase its utility in recombinant AAV vectors which have a size restricted packaging capacity of ~4.9 kb. The reduction in nucleotide length of the Ple305 (2,596 bp) promoter construct relied on bioinformatics analyses to identify regions that were less likely to contribute to regulatory function within the regulatory regions. The Ple305 construct (2,596 bp) combines a basal promoter element of 408 bp (SEQ ID NO: 2) with a conserved element with putative regulatory function of 897 bp (SEQ ID NO: 3) which was derived from regulatory element 8 shown in FIG. 3 and two intergenic regulatory regions of 340 bp (SEQ ID NO: 4) and 951 bp (SEQ ID NO: 5) which were derived from regulatory elements 10 and 11, respectively as shown in FIG. 3. The design of Ple305 is based, in part, on the identification of regions of conservation between the human genome and the mouse homolog (as shown in FIG. 4) and table 1 provides a list of the conserved regions within the Ple305 promoter (SEQ ID NO:1).

TABLE 1

List of conserved regions in the human OLIG1-based Mini-Promoter Ple305 (SEQ ID NO: 1). The "start" and "end" coordinates of the regions are relative to the full sequence of the Mini-Promoter. Conservation is determined by alignment of the human sequence and its mouse homolog using a threshold on the percentage of identity of 61%.

| Start (relative to SEQ ID NO: 1) | End (relative to SEQ ID NO: 1) | Invariant sequence type | Encompassing SEQ ID NO |
|---|---|---|---|
| 1 | 22 | Conserved sequence | 3 |
| 196 | 349 | Conserved sequence | 3 |
| 731 | 897 | Conserved sequence | 3 |
| 979 | 1223 | Conserved sequence | 4 |
| 1239 | 1263 | Conserved sequence | 5 |
| 1269 | 1928 | Conserved sequence | 5 |
| 2014 | 2160 | Conserved sequence | 5 |
| 2334 | 2516 | Conserved sequence | 2 |

The Mini-Promoter design is also dependent on the identification and selection of DNA regions that are likely to contribute to the regulation and transcriptional activity of a promoter. With respect to the human genome reference sequence and to the previously described Ple151 mini-promoter, the basal promoter of Ple305 (SEQ ID NO: 2) was shortened relative to Ple151 but regions that are predicted to contain enhancer elements and transcription start sites were maintained (FIG. 5). In addition, certain base-pair modifications were introduced into the basal promoter sequence (SEQ ID NO: 2) to improve the TATA-box and the upstream B recognition elements, which are known to facilitate binding of important transcription factors. These motifs were mutated to represent the consensus sequence binding profile of the two transcription factors, and thereby introducing 3 non-contiguous single bp mutations that are not observed in the human genome reference sequence and serve to strengthen the promoter activity (FIG. 5 and FIG. 6).

FIG. 7 shows the bioinformatics analysis for the regulatory element 8 (SEQ ID NO: 3), compared to the previously described to Ple151 promoter. The regulatory element 8 within the Ple305 (SEQ ID NO: 1) Mini-Promoter was reduced in size while retaining regions that are predicted to contain transcription factor binding sites. FIG. 8 shows the bioinformatic analysis for the regulatory element 10 (SEQ ID NO: 4) that was also reduced in size as compared to the previous Ple151 Mini-Promoter to remove areas of lower conservation between the human genome sequence and the mouse homolog, while maintaining enhancer and promoter regions. The regulatory element 10 (SEQ ID NO: 4) also contains an additional guanine residue relative to the human reference sequence. FIG. 9 shows the bioinformatic analysis for the regulatory element 11 (SEQ ID NO: 5) that was reduced in size as compared to Ple151 (SEQ ID NO: 6). Regions of lower levels of conservation were selected for removal using conservation levels across 100 vertebrates and between the human and mouse homologs. In addition, the regulatory element 11 (SEQ ID NO: 5) contains 5 mismatches relative to the reference sequence. To our knowledge, these are not previously described polymorphisms in the human population, and constitute non-native sequence alterations.

Example 2—Expression of lacZ in Brain with the Ple305 Mini-Promoter Construct

The Ple305 construct was tested in recombinant single-stranded adeno-associated virus serotype 9 (rAAV9 or ssAAV9) driving the icre recombinase reporter. Mice were injected intravenously with virus at post-natal day 0 (P0) as described elsewhere (Foust, Nurre et al. 2009). Expression was analyzed P21 and P56 via recombination of the reporter locus Gt(ROSA26)Sor$^{mSor1}$ (Soriano 1999). Once recombined, this locus expressed the β-galactosidase (lacZ gene) enzyme. Histochemical reaction with the X-gal substrate results in blue signal where the reporter is expressed.

As shown in FIG. 10, Ple305-driven icre expression was detected via lacZ immunohistochemistry throughout many brain regions, as expected for brain oligodendrocytes. In particular, there are puffy processes resembling oligodendrocyte morphology in the cortex and brainstem.

Example 3—Expression of EmGFP in Brain, Spinal Cord, and Dorsal Root Ganglion with the Ple305 Mini-Promoter Construct The Ple305 construct was tested in recombinant single-stranded adeno-associated virus serotype 9 (rAAV9 or ssAAV9) driving the EmGFP reporter. Mice were injected intravenously with virus at post-natal day 4 (P4) as described elsewhere (Foust, Nurre et al. 2009). Expression was analyzed P32 via antibody detection of GFP (green).

As shown in FIG. 11, Ple305-driven EmGFP expression was detected via GFP immunohistology throughout many brain regions, as expected for brain oligodendrocytes. In particular, there are puffy processes resembling oligodendrocyte morphology in the cortex, spinal core, and dorsal root ganglion.

Arnett, H. A., S. P. Fancy, et al. (2004). "bHLH transcription factor Olig1 is required to repair demyelinated lesions in the CNS." *Science* 306(5704): 2111-2115.

Balasubramaniyan, V., N. Timmer, et al. (2004). "Transient expression of Olig1 initiates the differentiation of neural stem cells into oligodendrocyte progenitor cells." *Stem Cells* 22(6): 878-882.

Brena, R. M., C. Morrison, et al. (2007). "Aberrant DNA methylation of OLIG1, a novel prognostic factor in non-small cell lung cancer." *PLoS Med* 4(3).

Bronson, S. K., E. G. Plaehn, et al. (1996). "Single-copy transgenic mice with chosen-site integration." *Proc Natl Acad Sci USA* 93(17): 9067-9072.

Burton, A. *Olig1 needed for remyelination*, Lancet Neurol. 2005 February; 4(2):80.

Chakrabarti, L., T. K. Best, et al. (2010). "Olig1 and Olig2 triplication causes developmental brain defects in Down syndrome." *Nat Neurosci* 13(8): 927-934.

Foust, K. D., E. Nurre, et al. (2009). "Intravascular AAV9 preferentially targets neonatal neurons and adult astrocytes." *Nat Biotech* 27(1): 59-65.

Friedli, M., I. Barde, et al. (2011). "A Systematic Enhancer Screen Using Lentivector Transgenesis Identifies Conserved and Non-Conserved Functional Elements at the Olig1 and Olig2 Locus." *PLoS ONE* 5(12): e15741.

Gong, X., T. Lin, et al. (2008). "Olig1 is downregulated in oligodendrocyte progenitor cell differentiation." *Neuroreport* 19(12): 1203-1207.

Goris, A., T. W. Yeo, et al. *Novel Olig 1-coding variants and susceptibility to multiple sclerosis*, J Neurol Neurosurg Psychiatry. 2006 November; 77(11):1296-7. Epub 2006 Jul. 4.

Hoang-Xuan, K., L. Aguirre-Cruz, et al. (2002). "OLIG-1 and 2 gene expression and oligodendroglial tumours." *Neuropathol Appl Neurobiol* 28(2): 89-94.

Jasin, M., M. E. Moynahan, et al. (1996). "Targeted transgenesis." *Proc Natl Acad Sci USA* 93(17): 8804-8808.

Liu, Y., P. Jiang, et al. (2011). "OLIG gene targeting in human pluripotent stem cells for motor neuron and oligodendrocyte differentiation." *Nat Protoc* 6(5): 640-655.

Lu, Q. R., D. Yuk, et al. (2000). "Sonic hedgehog—regulated oligodendrocyte lineage genes encoding bHLH proteins in the mammalian central nervous system." *Neuron* 25(2): 317-329.

Maire, C. L., A. Wegener, et al. (2010). "Gain-of-function of Olig transcription factors enhances oligodendrogenesis and myelination." *Stem Cells* 28(9): 1611-1622.

Othman, A., D. M. Frim, et al. (2011). "Olig1 is expressed in human oligodendrocytes during maturation and regeneration." *Glia* 59(6): 914-926.

Portales-Casamar, E., D. J. Swanson, et al. (2010). "A regulatory toolbox of MiniPromoters to drive selective expression in the brain." *Proceedings of the National Academy of Sciences of the United States of America* 107(38): 16589-16594.

Soriano, P. (1999). "Generalized lacZ expression with the ROSA26 Cre reporter strain." *Nat Genet* 21(1): 70-71.

van der Weyden, L., D. J. Adams, et al. (2002). "Tools for targeted manipulation of the mouse genome." *Physiol Genomics* 11(3): 133-164.

Whitman, L. M., C. A. Blanc, et al. (2012). "Olig1 function is required for remyelination potential of transplanted neural progenitor cells in a model of viral-induced demyelination." *Exp Neurol* 235(1): 380-387.

Wu, Y., J. P. Richard, et al. (2012). "Regulation of glioblastoma multiforme stem-like cells by inhibitor of DNA binding proteins and oligodendroglial lineage-associated transcription factors." *Cancer Sci* 103(6): 1028-1037.

Zhou, Q., S. Wang, et al. (2000). "Identification of a novel family of oligodendrocyte lineage-specific basic helix-loop-helix transcription factors." *Neuron* 25(2): 331-343.

What is claimed is:

1. An isolated polynucleotide comprising an OLIG1 mini-promoter wherein the OLIG1 mini-promoter comprises one or more OLIG1 regulatory elements with at least 95% sequence identity to one, two or all of SEQ ID NOs: 3-5 operably joined to an OLIG1 basal promoter with at least 95% sequence identity to SEQ ID NO: 2 through a non-native spacing between the regulatory elements and the basal promoter, wherein the OLIG1 mini-promoter has at least 95% sequence identity to SEQ ID NO: 1.

2. The isolated polynucleotide of claim 1, operably linked to an expressible sequence.

3. A vector comprising the isolated polynucleotide of claim 1.

4. An isolated cell comprising the vector of claim 3.

5. The cell of claim 4, wherein the cell is a stem cell, a neural stem cell, a neural progenitor cell, an oligodendrocyte precursor cell, neuron, glial cell, astrocyte, or an oligodendrocyte.

6. A method of expressing a sequence of interest, the method comprising operably linking the sequence of interest to the polynucleotide of claim 1; and introducing the operably linked sequence of interest into a cell permissive for expression from the OLIG1 mini-promoter.

7. The method of claim 6, wherein the cell is a neural cell or a progenitor thereof.

8. A method of treatment of a subject having a disease or condition of the brain, the method comprising administering to the subject a therapeutically effective dose of a composition comprising the polynucleotide of claim 1 operably linked to an expressible therapeutic sequence.

* * * * *

```
                        SEQUENCE LISTING

<160> NUMBER OF SEQ ID NOS: 6

<210> SEQ ID NO 1
<211> LENGTH: 2596
<212> TYPE: DNA
<213> ORGANISM: Artificial sequence
<220> FEATURE:
<223> OTHER INFORMATION: synthetic polynucleotide

<400> SEQUENCE: 1
cactgagtta atatttccag gtcagagcgc ctccgagaga aaaaggcggt ggccttggag      60
ctctggtctc cttaactgca ccctgggaag tcttcacacg gcctttcttc ccctggtggt     120
ctaatctgga gtcagatcca gccgtcagct cttacagacg gggaaggacc gggagccaac     180
gggaaaacaa caggtgagct tgtgaacaag tccccttctg tgtctcgggc agggtgtctg     240
cccgggcaac cgtggggctg cactgacttc cagaaccttc tgcctctgca ggtgttttag     300
gaacttggcc tcagcgcttc agtgacccat attttattac ctttcaggtt tctataattc     360
atcattcact cctttctgaa aacctagaat gaaaagttt  agcagctcag cgccgcggcc     420
tctctccatt ctctccccaa acacatcggc ctgtttgttc tctttcatcc ccgctcttcc     480
tgttgcattc tgccggttca atggggaagg agtgaaaccg gatggctgga cccagtgcgg     540
ggaaatgact tcagagccac ctttgtttcc ctcattcctt tgagcgcact tggccctgcg     600
tctctatgaa agggcttgtt tgaaccattc ggaacatcca gcaagccaga gatgctgcgg     660
ccagaaccgc tcgcatcttt tcaggctgcc tgagactctg ggttaaactg ccaaattttt     720
gcaacaaaac taaccatgac attggacatt gtgttataaa ttagccacag ccttccaagc     780
aaattgtctc tttttattgt atcagtgtaa gcctcggaaa catttggctt cagctactac     840
cttcagggag gctcagagga tattttgtt  ctgccccaaa ccaactcttc agacaccacc     900
ttccttgtcc tcacgcttga ctagcagaca atgggttctt cagaagccac agcatttcag     960
ctgttttggc cccagaggcc acaagctgac tgcatgtcat tctccaccag cagagcgtca    1020
cctcggggta gctccaaaca gtatcaaccg gtttgtggtg agtggataaa caccaggctg    1080
ggtgaatgaa gtcacaggct gagtcatcct ctgcacatgg gggctgaatg gggctcagtc    1140
aggcccagag gagcctcccc ggcaaggtgc tgggggccag gctctccctg ccagtgaggc    1200
tggggtccgt ccccaatagt cattcctttg gccaacagaa atgataaggc agacaaatgg    1260
aagatcaatg aagcaacatc gtggcaataa tgcaattggt cctgccgtag tcatgaacat    1320
gtaaataaca agacagcaat aagaagaccc cagactctgc ctagaaacaa aatattcagc    1380
ctgttgttgt tgtttcttat tgcaggattt tgagtggaaa agtagttcca cttgtcaatc    1440
agctacgttg cagggctaa  tagattctgg tgtttaggga ggtcaacacg gaatttaatt    1500
taacatctca caatacaccc acatgcccag aaaatgtgga cagcttgata gggttcactg    1560
agccaaagaa gcaagaccca aacagtgcat taatgtatag gggaagaata gttgcaatca    1620
gccccttgtg aattggacag agggcttgga gatgaagcaa ttatcagcca tcggggatta    1680
atagtaaagt gtgaatacca agctgtatat gttaggggca gaatatgttg cctatagaaa    1740
acaacaaagg acgtttctta ctattaagtg agattaaacg taatggcctg atttaatcac    1800
aaaggcagaa ttaaattcag atggcaactt caaagtggac acaggaacac aggccactgc    1860
```

```
ttacatttac atatagctgg catagcttgg cctgcaacac aataggataa agtttctttg    1920
gccacttaaa caattttcta ttcttcacct ttttctttt  ttcttttttt tttcttttgt    1980
gggtgtgtgt gtgtgtgtgt gtgtgtgtga acactcactg tatttattcc ccaattgcat    2040
ttagttagta agaaggagct aagtgttata tttattcatg gaggctataa ctgttaattc    2100
ttccaaattg tgaaaaaaaa gcctcatagg gtcaataaga acagagtagt tataatcaga    2160
ttgtcaccaa aaagaaaaa  gaagaaaaag gttgttttg  agtagacagt tgctggagga    2220
aggcacgtga gttgcagcct gaccagtgcg accagtcctc cttcaacagc ccgcttgcc     2280 ttgaaaaggc gcccttactc cgctcagggg gcctgtcccg cgcggctggc acaggcgctc    2340
acaataacct cctaaagcgg tgccagccgc acctccgcgc ggccccggca caagcagcca    2400
atgaacacgc ggctgcgccc ggcctcgcgc ctccattggc tgcgcccgc  cacccgctgc    2460 cccgcaggtt cccacgccgg gtataaatgg gtagggcgcg ggccagggcc ccaccatcgt    2520
ttccccgcgc gcaggtccgc ggggagggc  ggcctgccga ccggcccacc ccagggcgtt    2580
cctgaagggc gtcctc                                                    2596

<210> SEQ ID NO 2
<211> LENGTH: 408
<212> TYPE: DNA
<213> ORGANISM: Artificial sequence
<220> FEATURE:
<223> OTHER INFORMATION: synthetic polynucleotide

<400> SEQUENCE: 2
aggttgtttt tgagtagaca gttgctggag gaaggcacgt gagttgcagc ctgaccagtg     60
cgaccagtcc tccttcaaca gccccgcttg ccttgaaaag gcgcccttac tccgctcagg    120
gggcctgtcc cgcgcggctg gcacaggcgc tcacaataac ctcctaaagc ggtgccagcc    180
gcacctccgc gcggccccgg cacaagcagc caatgaacac gcggctgcgc ccggcctcgc    240
gcctccattg gctgcgcccc gccacccgct gccccgcagg ttcccacgcc gggtataaat    300
gggtagggcg cgggccaggg ccccaccatc gtttccccgc gcgcaggtcc gcggggaggg    360
gcggcctgcc gaccggccca ccccagggcg ttcctgaagg gcgtcctc                 408

<210> SEQ ID NO 3
<211> LENGTH: 897
<212> TYPE: DNA
<213> ORGANISM: Artificial sequence
<220> FEATURE:
<223> OTHER INFORMATION: synthetic polynucleotide

<400> SEQUENCE: 3
cactgagtta atatttccag gtcagagcgc ctccgagaga aaaggcggt  ggccttggag     60 ctctggtctc cttaactgca ccctgggaag tcttcacacg gcctttcttc ccctggtggt    120
ctaatctgga gtcagatcca gccgtcagct cttacagacg gggaaggacc gggagccaac    180
gggaaaacaa caggtgagct tgtgaacaag tccccttctg tgtctcgggc agggtgtctg    240
cccgggcaac cgtggggctg cactgacttc agaaccttc  tgcctctgca ggtgttttag    300
gaacttggcc tcagcgcttc agtgacccat attttattac ctttcaggtt tctataattc    360
atcattcact cctttctgaa aacctagaat gaaaaagttt agcagctcag cgccgcggcc    420
tctctccatt ctctccccaa acacatcggc ctgtttgttc tctttcatcc ccgctcttcc    480
tgttgcattg tgccggttca atggggaagg agtgaaaccg gatggctgga cccagtgcgg    540
ggaaatgact tcagagccac ctttgtttcc ctcattcctt tgagcgcact tggccctgcg    600
```

```
tctctatgaa agggcttgtt tgaaccattc ggaacatcca gcaagccaga gatgctgcgg    660
ccagaaccgc tcgcatcttt tcaggctgcc tgagactctg ggttaaactg ccaaattttt    720
gcaacaaaac taaccatgac attggacatt gtgttataaa ttagccacag ccttccaagc    780
aaattgtctc ttttattgt atcagtgtaa gcctcggaaa catttggctt cagctactac    840
cttcagggag gctcagagga tattttgtt ctgccccaaa ccaactcttc agacacc       897
```

```
<210> SEQ ID NO 4
<211> LENGTH: 341
<212> TYPE: DNA
<213> ORGANISM: Artificial sequence
<220> FEATURE:
<223> OTHER INFORMATION: synthetic polynucleotide

<400> SEQUENCE: 4
accttccttg tcctcacgct tgactagcag acaatgggtt cttcagaagc cacagcattt     60
cagctgtttt ggccccagag gccacaagct gactgcatgt cattctccac cagcagagcg    120
tcacctcggg gtagctccaa acagtatcaa ccggtttgtg gtgagtggat aaacaccagg    180
ctgggtgaat gaagtcacag gctgagtcat cctctgcaca tgggggctga atggggctca    240
gtcaggccca gaggagcctc cccggcaagg tgctggggc caggctctcc ctgccagtga     300
ggctggggtc cgtccccaat agtcattcct ttggccaaca g                       341
```

```
<210> SEQ ID NO 5
<211> LENGTH: 950
<212> TYPE: DNA
<213> ORGANISM: Artificial sequence
<220> FEATURE:
<223> OTHER INFORMATION: synthetic polynucleotide

<400> SEQUENCE: 5
aaatgataag gcagacaaat ggaagatcaa tgaagcaaca tcgtggcaat aatgcaattg     60
gtcctgccgt agtcatgaac atgtaaataa caagacagca ataagaagac cccagactct    120
gcctagaaac aaaatattca gcctgttgtt gttgtttctt attgcaggat tttgagtgga    180
aaagtagttc cacttgtcaa tcagctacgt tgcaggggct aatagattct ggtgtttagg    240
gaggtcaaca cggaatttaa tttaacatct cacaatacac ccacatgccc agaaaatgtg    300
gacagcttga tagggttcac tgagccaaag aagcaagacc caaacagtgc attaatgtat    360
aggggaagaa tagttgcaat cagccccttg tgaattggac agagggcttg gagatgaagc    420
aattatcagc catcggggat taatagtaaa gtgtgaatac caagctgtat atgttagggg    480
cagaatatgt tgcctataga aaacaacaaa ggacgtttct tactattaag tgagattaaa    540
cgtaatggcc tgatttaatc acaaaggcag aattaaattc agatggcaac ttcaaagtgg    600
acacaggaac acaggccact gcttacattt acatatagct ggcatagctt ggcctgcaac    660
acaataggat aaagtttctt tggccactta acaattttc tattcttcac ctttttcttt    720
ttttcttttt ttttcttttt gtgggtgtgt gtgtgtgtgt gtgtgtgtgt gaacactcac    780
tgtatttatt ccccaattgc atttagttag taagaaggag ctaagtgtta tatttattca    840
tggaggctat aactgttaat tcttccaaat tgtgaaaaaa aagcctcata gggtcaataa    900
gaacagagta gttataatca gattgtcacc aaaaaagaaa aagaagaaaa               950
```

```
<210> SEQ ID NO 6
<211> LENGTH: 3042
<212> TYPE: DNA
```

<213> ORGANISM: Artificial sequence
<220> FEATURE:
<223> OTHER INFORMATION: synthetic polynucleotide

<400> SEQUENCE: 6

```
tgttcaactc ggatagtcct caccactgag ttaatatttc caggtcagag cgcctccgag      60
agaaaaaggc ggtggccttg gagctctggt ctccttaact gcaccctggg aagtcttcac     120
acggcctttc ttcccctggt ggtctaatct ggagtcagat ccagccgtca gctcttacag     180
acggggaagg accgggagcc aacgggaaaa caacaggtga gcttgtgaac aagtcccctt     240
ctgtgtctcg ggcaggtgt ctgcccgggc aacctgtgggg ctgcactgac ttccagaacc     300
ttctgcctct gcaggtgttt taggaacttg gcctcagcgc ttcagtgacc catattttat     360
tacctttcag gtttctataa ttcatcattc actcctttct gaaaacctag aatgaaaaag     420
tttagcagct cagcgccgcg gcctctctcc attctctccc caaacacatc ggcctgtttg     480
ttctctttca tccccgctct tcctgttgca ttctgccggt tcaatgggga aggagtgaaa     540
ccggatggct ggacccagtg cggggaaatg acttcagagc caccctttgtt tccctcattc     600
ctttgagcgc acttggccct gcgtctctat gaaagggctt gtttgaacca ttcggaacat     660
ccagcaagcc agagatgctg cggccagaac cgctcgcatc ttttcaggct gcctgagact     720
ctgggttaaa ctgccaaatt tttgcaacaa aactaaccat gacattggac attgtgttat     780
aaattagcca cagccttcca agcaaattgt ctcttttat tgtatcagtg taagcctcgg     840
aaacatttgg cttcagctac taccttcagg gaggctcaga ggatatttt gttctgcccc     900
aaaccaactc ttcagacacc gagttgcatg tgctaatacc catatcttca ttcacagtta     960
ttcttatcac actccctctg agaacctctg tcagttatgt tctatttctc tgcctcccag    1020
aaccttcctt gtcctcacgc ttgactagca gacaatgggt tcttcagaag ccacagcatt    1080
tcagctgttt tggccccaga ggccacaagc tgactgcatg tcattctcca ccagcagagc    1140
gtcacctcgg ggtagctcca aacagtatca accggtttgt ggtgagtgga taaacaccag    1200
gctgggtgaa tgaagtcaca ggctgagtca tcctctgcac atgggggctg aatggggctc    1260
agtcaggccc agaggagcct ccccggcaag gtgctgggggg ccaggctctc cctgccagtg    1320
aggctggggt ccgtccccaa tagtcattcc tttggccaac aaacacttat tgagcgccca    1380
cctagctctt caagtcgcag ataacagtga aggccctaag actcaccatc caaaacagtt    1440
ttggaaaaaa accaaagaag agaaaataat ttcaaaccctt aaagcaatgc atggtgattc    1500
tctgggggt ctaagaattt ctcccagaga aatgataagg cagacaaatg gaagatcaat    1560
gaagcaacat cgtggcaata atgcaattgg tcctgccgta gtcatgaaca tgtaaataac    1620
aagacagcaa taagaagacc ccagactctg cctagaaaca aaatattcag cctgttgttg    1680
ttgtttctta ttgcaggatt ttgagtggaa aagtagttcc acttgtcaat cagctacgtt    1740
gcaggggcta atagattctg tgtgtttaggg aggtcaacac ggaatttaat ttaacatctc    1800
acaatacacc cacatgccca gaaaatgtgg acagcttgat agggttcact gagccaaaga    1860
agcaagaccc aaacagtgca ttaatgtata ggggaagaat agttgcaatc agccccttgt    1920
gaattggaca gagggcttgg agatgaagca attatcagcc atcggggatt aatagtaaag    1980
tgtgaatacc aagctgtata tgttaggggc agaatatgtt gcctatagaa aacaacaaag    2040
gacgtttctt actattaagt gagattaaac gtaatggcct gatttaatca caaaggcaga    2100
attaaattca gatggcaact tcaaagtgga cacaggaaca caggccactg cttacattta    2160
catatagctg gcatagcttg gcctgcaaca caataggata aagtttcttt ggccacttaa    2220
```

```
acaattttct attcttcacc tttttctttt tttcttttt ttttctttg tgggtgtgtg      2280 tgtgtgtgtg tgtgtgtgtg aacactcact gtatttattc cccaattgca tttagttagt      2340
aagaaggagc taagtgttat atttattcat ggaggctata actgttaatt cttccaaatt      2400
gtgaaaaaaa agcctcatag ggtcaataag aacagagtag ttataatcag attgtcacca      2460
aaaaagaaaa agaagaaaaa caattaaaca aaacaaacaa acaaaacttt ctagagtgaa      2520
cagtgtcttc taactttctc tcccttcaac ttaagaattc agctcttgag gacataagac      2580
ggtaaatttt atgttatgaa tatgtgatca cagttaaaaa aaaatatgag ggaggttgtt      2640
tttgagtaga cagttgctgg aggaaggcac gtgagttgca gcctgaccag tgcgaccagt      2700
cctccttcaa cagccccgct tgccttgaaa aggcgccctt actccgctca gggggcctgt      2760
cccgcgcggc tggcacaggc gctcacaata acctcctaaa gcggtgccag ccgcacctcc      2820
gcgcggcccc ggcacaagca gccaatgaac acgcggctgc gcccggcctc gcgcctccat      2880
tggctgcgcc ccgccacccg ctgccccgca ggttcccaag ccgggtttaa aggggtaggg      2940
cgcgggccag ggccccacca tcgtttcccc gcgcgcaggt ccgcggggag gggcggcctg      3000
ccgaccggcc cacccaggg cgttcctgaa gggcgtcctc gg                         3042
```